United States Patent
Peters et al.

(10) Patent No.: US 7,098,339 B2
(45) Date of Patent: Aug. 29, 2006

(54) PROCESSES FOR THE PRODUCTION OF ORGANOMETALLIC COMPOUNDS

(75) Inventors: David Walters Peters, North Tonawanda, NY (US); Michael Thomas Mosscropp, III, Buffalo, NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 11/036,027

(22) Filed: Jan. 18, 2005

(65) Prior Publication Data

US 2006/0161014 A1    Jul. 20, 2006

(51) Int. Cl.
C07F 5/06 (2006.01)
(52) U.S. Cl. .............................. 546/11; 548/402; 549/3
(58) Field of Classification Search ................. 546/11; 548/402; 549/3
See application file for complete search history.

(56) References Cited

U.S. PATENT DOCUMENTS

| | | | |
|---|---|---|---|
| 6,121,443 A | 9/2000 | Shin | 544/64 |
| 6,143,357 A | 11/2000 | Shin et al. | 427/126.1 |
| 6,399,772 B1 | 6/2002 | Shin et al. | 544/64 |
| 6,432,820 B1 | 8/2002 | Lee et al. | 438/677 |
| 2002/0132469 A1 | 9/2002 | Lee et al. | 438/628 |
| 2002/0160602 A1 | 10/2002 | Lee et al. | 438/677 |

FOREIGN PATENT DOCUMENTS

JP    2000 323481    11/2000

OTHER PUBLICATIONS

Marlett et al., "Dimethylethylamine-Alane and N-Methylpyrrolidine-Alane. A convenient Synthesis of Alane, a Useful Selective Reducing Agent in organic Synthesis", *J. Org. Chem.* 1990, 55, 2968-2969.

Ruff et al., "The Amine Complexes of Aluminium Hydride." I, *J. Amer. Chem. Soc.*, 1960, 82, 2141.

Kovar et al., "Trihydrido(Trimethylamine)Aluminum and (Diethylamino)Hydridoaluminum Complexes", *Inorg. Synth.*, 1977, 17, 36.

Frigo et al., "Preparation and Properties of Alane Dimethylethylamine, a Liquid Precursor for MOCVD", *Chem. Mater.*, 1994, 6, 190.

*Primary Examiner*—Porfirio Nazario-Gonzalez
(74) *Attorney, Agent, or Firm*—Gerald L. Coon

(57) ABSTRACT

This invention relates to processes for the production of organometallic compounds represented by the formula $H_3Al:L_n$ wherein L is one or more Lewis bases capable of providing an unshared electron pair to the aluminum and n is 1 or 2, which comprise (a) forming a first solution of an alkali metal aluminum hydride and a Lewis base in an ethereal solvent, (b) adding to said first solution an aluminum halide in an ethereal solvent under reaction conditions sufficient to produce a second solution comprising said organometallic compound, and (c) separating said organometallic compound from said second solution. The organometallic compounds are useful in semiconductor applications as chemical vapor or atomic layer deposition precursors for film depositions.

20 Claims, No Drawings

US 7,098,339 B2

PROCESSES FOR THE PRODUCTION OF ORGANOMETALLIC COMPOUNDS

FIELD OF THE INVENTION

This invention relates to processes for the production of organometallic compounds represented by the formula $H_3Al:L_n$ wherein L is one or more Lewis bases capable of providing an unshared electron pair to the aluminum and n is 1 or 2. The organometallic compounds are useful in semiconductor applications as chemical vapor or atomic layer deposition precursors for film depositions.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition organometallic compound, is decomposed thermally, chemically, photochemically or by plasma activation, to form a thin film having a desired composition. Typically, a chemical vapor deposition organometallic precursor can be contacted with a substrate that is heated to a temperature higher than the decomposition temperature of the precursor, to form a metal or metal oxide film on the substrate.

For example, aluminum interconnects are used in the manufacture of DRAM type microchips and flash memory devices. Aluminum is a good conductor of electricity and is easy to deposit by chemical vapor deposition. Aluminum oxide (alumina) is an insulator used in microchip manufacture. A popular precursor for aluminum and alumina chemical vapor deposition is trimethylaluminum. Trimethylaluminum, however, is extremely pyrophoric and difficult to handle. 1-Methylpyrrolidinealane (MPA) is a free flowing, non-pyrophoric precursor to aluminum and alumina with good stability, a low decomposition temperature and a high vapor pressure.

The synthetic processes utilized to generate organometallic precursors are highly important, and must insure safety, high purity, throughput, and consistency. However, the air-sensitive nature of the starting materials make the synthesis of organometallic precursors more challenging. When starting materials are solids, it makes air-free transfer more difficult. Employing reactants that cannot be solvated can cause mixing and handling problems in the process, especially in large scale production. Furthermore, the use of reactants that cannot be solvated can lead to lower product yields. Therefore, developing a methodology for producing organometallic precursors that addresses the aforementioned potential hold-ups would be beneficial toward establishing the production of these materials for use in the electronics industry.

Current manufacturing methods for 1-methylpyrrolidinealane involve the use of various solvents. For example, U.S. Pat. No. 6,143,357 discloses a process for making organometallic compounds, e.g., 1-methylpyrrolidinealane, by forming a suspension of aluminum trichloride and lithium aluminum hydride in hexane or pentane and adding a Lewis base, e.g., 1-methylpyrrolidine, to the suspension. Hexane is an OSHA toxic chemical with a PEL of 500 ppm. A spill of one pound of n-hexane requires notification of the National Response Center. Both lithium aluminum hydride and aluminum trichloride are solids and neither is soluble in pentane or hexane. This leads to difficulties in large scale production (handling of air sensitive solids) and lower yields.

Marlett and Park (Marlett, E. M.; Park, W. S. *J. Org. Chem.*, 1990, 55, 2968) reported the synthesis of 1-methylpyrrolidinealane by the action of N-methylpyrrolidine on lithium aluminum hydride in toluene. A reactive solid (trilithium aluminum hexahydride) was produced as a byproduct.

Frigo and van Eijden (Frigo, D. M.; van Eijden, G. J. M. *Chem. Mater.*, 1994, 6, 190) reported a process for making amine adducts of alane by adding a stoichiometric amount of an amine to a slurry of lithium aluminum hydride and aluminum chloride in the presence of an alkane solvent, e.g., pentane. Frigo and van Eijden state that the use of ether solvents "is very likely to give contamination of the end product by the ether, which could lead to incorporation of oxygen in the Al-containing layers."

Amine adducts of alane have been used in organic synthesis for the reduction of organic compounds to alcohols and amines. As such, there are several published methods of making alane amines. A common method is the reaction of lithium aluminum hydride with trialkylammonium chlorides as reported by Ruff and Hawthorne (Ruff, J. K.; Hawthorne, M. F. *J. Amer. Chem. Soc.*, 1960, 82, 2141) using ethereal solvents or Kovar and Callaway (Kovar, R. A.; Callaway, J. O. *Inorg. Synth.*, 1977, 17, 36) using aromatic solvents. Ruff and Hawthorne employ solid reagent addition in their experimental methods. Also, the hydrochloric acid salt of N-methylpyrrolidine is insoluble in ethereal solvents.

The prior art processes used to produce 1-methylpyrrolidinealane have various disadvantages as discussed above. Therefore, a need continues to exist for new processes for making organometallic precursors that are safer (e.g., no hazardous solvents), allow for easier handling of reactants (e.g., allow the solid reagents to be dissolved and transferred in solution through the use of metering pumps), give higher product yields and permit easier scale up for production quantities of organometallic compounds. It would therefore be desirable in the art to provide new processes for making organometallic compounds that address these needs.

SUMMARY OF THE INVENTION

This invention relates to a process for preparing an organometallic compound represented by the formula $H_3Al:L_n$ wherein L is one or more Lewis bases capable of providing an unshared electron pair to the aluminum and n is 1 or 2, said process selected from the following:

(1) a process for preparing said organometallic compound comprising (a) forming a first solution of an alkali metal aluminum hydride and a Lewis base in an ethereal solvent, (b) adding to said first solution an aluminum halide in an ethereal solvent under reaction conditions sufficient to produce a second solution comprising said organometallic compound, and (c) separating said organometallic compound from said second solution;

(2) a process for preparing said organometallic compound comprising (a) forming a first solution of an aluminum halide and a Lewis base in an ethereal solvent, (b) adding to said first solution an alkali metal aluminum hydride in an ethereal solvent under reaction conditions sufficient to produce a second solution comprising said organometallic compound, and (c) separating said organometallic compound from said second solution; and (3) a process for preparing said organometallic compound comprising (a) reacting an aluminum halide and an alkali metal aluminum hydride in the presence of an ethereal solvent and under reaction conditions sufficient to produce a first solution, (b) adding to said first solution a Lewis base optionally in an ethereal solvent under reaction conditions sufficient to produce a second solution comprising said organometallic compound, and (c) separating said organometallic compound from said second solution.

Ethereal solvents are normally avoided in the synthesis of semiconductor grade chemicals due to the difficulty in separating organometallic compounds from the solvent. It is well known that metallic compounds form a complex with ethers that will even survive distillation. However, in the process of this invention, the final product is a complex between an amine and the metallic compound. Amines bind to metals more strongly than ethers do, so solvent removal is not a problem.

The invention has several advantages. For example, the process of this invention is useful in generating organometallic compound precursors that have varied chemical structures and physical properties. The process of this invention allows for all of the reagents to be handled in solution. This leads to easier scale up for production quantities and for automation through the use of metering pumps. The process of this invention affords high yields of organometallic compound precursors thereby providing significant economic advantages. Further, the process of this invention allows for the use of safer solvents.

DETAILED DESCRIPTION OF THE INVENTION

As indicated herein, this invention involves a process for preparing an organometallic compound represented by the formula $H_3Al:L_n$ wherein L is one or more Lewis bases capable of providing an unshared electron pair to the aluminum and n is 1 or 2, said process selected from the following:

(1) a process for preparing said organometallic compound comprising (a) forming a first solution of an alkali metal aluminum hydride and a Lewis base in an ethereal solvent, (b) adding to said first solution an aluminum halide in an ethereal solvent under reaction conditions sufficient to produce a second solution comprising said organometallic compound, and (c) separating said organometallic compound from said second solution;

(2) a process for preparing said organometallic compound comprising (a) forming a first solution of an aluminum halide and a Lewis base in an ethereal solvent, (b) adding to said first solution an alkali metal aluminum hydride in an ethereal solvent under reaction conditions sufficient to produce a second solution comprising said organometallic compound, and (c) separating said organometallic compound from said second solution; and (3) a process for preparing said organometallic compound comprising (a) reacting an aluminum halide and an alkali metal aluminum hydride in the presence of an ethereal solvent and under reaction conditions sufficient to produce a first solution, (b) adding to said first solution a Lewis base optionally in an ethereal solvent under reaction conditions sufficient to produce a second solution comprising said organometallic compound, and (c) separating said organometallic compound from said second solution.

The process is particularly well-suited for large scale production since it can be conducted using the same equipment, some of the same reagents and process parameters that can easily be adapted to manufacture a wide range of products. The method provides for the synthesis of organometallic compounds using a unique process where all manipulations can be carried out in a single vessel, and which route to the organometallic compounds does not require the isolation of any intermediate complexes.

The process of this invention is different from the prior art in the solvents that are employed, the way the reagents are mixed and the order of addition of the reagents. The process of this invention is safer (e.g., no hazardous solvents required) and readily lends itself to scale up for production synthesis.

This invention allows for all of the reagents to be handled in solution. This leads to easy scale up for production quantities and for automation through the use of metering pumps since solutions are easier to manipulate than slurries which allows for the use of metering pumps to transport the reagents in a production environment. It also results in higher yield (~25%) than previously published methods. These factors translate to an economic advantage.

With higher yields compared to prior art methods, the process of this invention also avoids labor-intensive and waste generating material manipulations. The process of this invention allows for all of the reagents to be handled in solution. This leads to easier scale up for production quantities and for automation through the use of metering pumps. This method of this invention also eliminates the formation and isolation of intermediates, as well as reducing the amount of materials (e.g., chemical reagents, glassware) required substantially. Furthermore, because all transformations can occur in one vessel until the final product is isolated, all compounds (e.g., side-products) are confined to one location. The product yield can range from about 65 to 99% or greater, preferably from about 75 to 99% or greater, and more preferably from about 85 to 99% or greater.

The alkali metal aluminum hydride starting material may be selected from a wide variety of compounds known in the art. Illustrative alkali metal aluminum hydrides include lithium aluminum hydride, sodium aluminum hydride and the like. The alkali metal aluminum hydride starting material is preferably lithium aluminum hydride.

The concentration of the alkali metal aluminum hydride starting material can vary over a wide range, and need only be that minimum amount necessary to form a solution with a Lewis base in an ethereal solvent in process (1) above, react with a solution of an aluminum halide and a Lewis base in an ethereal solvent in process (2) above, or react with an aluminum halide in the presence of an ethereal solvent in process (3) above. In general, depending on the size of the solution or reaction mixture, alkali metal aluminum hydride starting material concentrations in the range of from about 1 millimole or less to about 1000 millimoles or greater, should be sufficient for most processes.

The aluminum halide starting material may be selected from a wide variety of compounds known in the art. Illustrative aluminum halides include aluminum chloride, aluminum bromide, aluminum iodide, aluminum fluoride, and the like. The aluminum halide starting material is preferably aluminum chloride.

The concentration of the aluminum halide starting material can vary over a wide range, and need only be that minimum amount necessary to react with a solution of an alkali metal aluminum hydride and a Lewis base in an ethereal solvent in process (1) above, form a solution with a Lewis base in an ethereal solvent in process (2) above, or react with an alkali metal aluminum hydride in the presence of an ethereal solvent in process (3) above. In general, depending on the size of the solution or reaction mixture, aluminum halide starting material concentrations in the range of from about 1 millimole or less to about 1000 millimoles or greater, should be sufficient for most processes.

The Lewis base starting material may be selected from a wide variety of compounds known in the art. Illustrative Lewis base compounds include, for example, thiophene, thiopyran, cyclic organic amines, and the like. Suitable cyclic organic amine starting materials include alkylaziridines, alkylazetidines, alkylpyrrolidines, alkylpiperidines, alkylhexamethyleneimines, alkylheptamethyleneimines and alkylpiperazines. Preferred Lewis base starting materials include, for example, 1-methylpyrrolidine, 1-butylpyrrolidine, 1,4-dimethylpyrrolidine, 1-methylpiperidine, 1-ethylpiperidine, 1,2,2,6,6-pentamethylpiperidine, 1,4-dimethylpiperazine, thiophene and thiopyran. The most preferred Lewis base is 1-methylpyrrolidine.

The concentration of the Lewis base starting material can vary over a wide range, and need only be that minimum amount necessary to form a solution with an alkali metal aluminum hydride in an ethereal solvent in process (1) above, form a solution with an aluminum halide in an ethereal solvent in process (2) above, or react with a solution of an alkali metal aluminum hydride and an aluminum halide in an ethereal solvent in process (3) above. In general, depending on the size of the solution or reaction mixture, Lewis base starting material concentrations in the range of from about 1 millimole or less to about 1000 millimoles or greater, should be sufficient for most processes.

The solvent employed in the method of this invention may be any ethereal solvent or mixtures of ethereal solvents, preferably diethyl ether, diisopropyl ether, di-n-propyl ether, di-n-butyl ether and tetrahydrofuran. Any suitable ethereal solvent which does not unduly adversely interfere with the intended reaction can be employed. Mixtures of one or more different ethereal solvents may be employed if desired. The amount of ethereal solvent employed is not critical to the subject invention and need only be that amount sufficient to solubilize the reaction components in the solution or reaction mixture and to provide for solubilized reagent addition in the process. In general, the amount of solvent may range from about 5 percent by weight up to about 99 percent by weight or more based on the total weight of the solution or reaction mixture starting materials. The use of ethereal solvents, e.g., diethyl ether, allows the reactants to be solvated which allows for better mixing and ease of handling through the use of metering pumps to move the process liquids.

Reaction conditions for the reaction of the aluminum halide in an ethereal solvent with the solution of an alkali metal aluminum hydride and a Lewis base in an ethereal solvent (i.e., process (1) above), such as temperature, pressure and contact time, may also vary greatly and any suitable combination of such conditions may be employed herein. The reaction temperature may be the reflux temperature of any of the aforementioned ethereal solvents, and more preferably between about $-80°$ C. to about $150°$ C., and most preferably between about $20°$ C. to about $80°$ C. Normally the reaction is carried out under ambient pressure and the contact time may vary from a matter of seconds or minutes to a few hours or greater. The stir time employed can range from about 0.1 to about 400 hours, preferably from about 1 to 75 hours, and more preferably from about 4 to 16 hours, for all steps.

Reaction conditions for the reaction of the alkali metal aluminum hydride in an ethereal solvent with the solution of an aluminum halide and a Lewis base in an ethereal solvent (i.e., process (2) above), such as temperature, pressure and contact time, may also vary greatly and any suitable combination of such conditions may be employed herein. The reaction temperature may be the reflux temperature of any of the aforementioned ethereal solvents, and more preferably between about $-80°$ C. to about $150°$ C., and most preferably between about $20°$ C. to about $80°$ C. Normally the reaction is carried out under ambient pressure and the contact time may vary from a matter of seconds or minutes to a few hours or greater. The stir time employed can range from about 0.1 to about 400 hours, preferably from about 1 to 75 hours, and more preferably from about 4 to 16 hours, for all steps.

Reaction conditions for the reaction of the aluminum halide with the alkali metal aluminum hydride in an ethereal solvent to produce a first solution and also the reaction of this first solution with a Lewis base in an ethereal solvent (i.e., process (3) above), such as temperature, pressure and contact time, may also vary greatly and any suitable combination of such conditions may be employed herein. The reaction temperature may be the reflux temperature of any of the aforementioned ethereal solvents, and more preferably between about $-80°$ C. to about $150°$ C., and most preferably between about $20°$ C. to about $80°$ C. Normally the reaction is carried out under ambient pressure and the contact time may vary from a matter of seconds or minutes to a few hours or greater. The stir time employed can range from about 0.1 to about 400 hours, preferably from about 1 to 75 hours, and more preferably from about 4 to 16 hours, for all steps.

The organometallic compounds prepared from the processes of this invention may be selected from a wide variety of compounds known in the art. For purposes of this invention, organometallic compounds include compounds represented by the formula $H_3Al:L_n$ wherein L is one or more Lewis bases capable of providing an unshared electron pair to the aluminum and n is 1 or 2. Illustrative organometallic compounds include, for example, 1-methylpyrrolidinealane, 1-methylpiperidinealane, 1-ethylpiperidinealane, 4-methylmorpholinealane and 1,4-dimethylpiperazinealane, and the like.

The method of this invention may utilize an in line filtration which pumps out the product solution leaving the undesired solids behind. An air-free bag filter may also be used. Alternatively, the solids may be allowed to settle and the supernatant can be removed without the need for a filtration. Solvent washings may be utilized to minimize any product loss due to transfer. Another, yet less preferred, method would simply entail removing all the contents, including solids, and distilling, or simply distilling directly from the reaction pot.

Once the relatively solid-free solution has been transferred to the distillation flask, the product may be distilled quite easily away from the reaction solvent and any undesired byproducts. Due to the fact that the method of this invention is performed outside a glovebox, the reaction can be readily scaled to kilogram levels.

For organometallic compounds prepared by the method of this invention, purification can occur through recrystallization, more preferably through extraction of reaction residue (e.g., hexane) and chromatography, and most preferably through sublimation and distillation.

Those skilled in the art will recognize that numerous changes may be made to the method described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

Many organometallic compound precursors described herein are liquid at room temperature and are well suited for preparing in-situ powders and coatings. For instance, a liquid organometallic compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

This invention also relates in part to a process for producing a film, coating or powder. The process includes the step of decomposing at least one organometallic compound precursor, thereby producing the film, coating or powder, as further described below.

Deposition processes described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of hafnium, hafnium oxides, hafnium silicates and hafnium aluminates, for instance, can be considered for fabricating metal electrodes, in particular as n-channel metal electrodes in logic, as capacitor electrodes for DRAM applications, and as dielectric materials.

The process also is suited for preparing layered films, wherein at least two of the layers differ in phase or composition. Examples of layered film include metal-insulator-semiconductor, and metal-insulator-metal.

In an embodiment, the invention is directed to a process that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metalorganic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The process of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the process of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The process of the invention can be conducted to deposit a film on a substrate that has a smooth, flat surface. In an embodiment, the process is conducted to deposit a film on a substrate used in wafer manufacturing or processing. For instance, the process can be conducted to deposit a film on patterned substrates that include features such as trenches, holes or vias. Furthermore, the process of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometers thick. Films that are less than 50 nanometer thick, for instance, films that have a thickness between about 20 and about 30 nanometer, also can be produced.

Organometallic compound precursors described above also can be employed in the process of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The process of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above an organometallic compound precursor can be used alone or in combination with one or more components, such as, for example, other organometallic precursors, inert carrier gases or reactive gases.

In a system that can be used in producing films by the process of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

EXAMPLE 1

Ethereal solutions of lithium aluminum hydride can be purchased from chemical suppliers. Before the reaction, a solution of aluminum trichloride in ether was made. This was done under an inert atmosphere. Aluminum trichloride was slowly added to the ether in order to control the temperature. Aluminum trichloride formed a complex with the ether and this complexation was exothermic.

4.32 grams of aluminum trichloride was dissolved in 65 milliliters of diethyl ether.

A 250 milliliter three necked flask was fitted with a magnetic stir bar, reflux condenser and rubber septa.

100 milliliters of a 1 molar solution of lithium aluminum hydride (95%) in ether was transferred into the flask.

15 milliliters of N-methylpyrrolidine was added to the lithium aluminum hydride in ether while stirring (preferably a 10% excess of N-methylpyrrolidine is added to ensure that the reaction goes to completion).

The rubber septa was replaced with a dropping funnel under a nitrogen purge and was purged with nitrogen for another minute.

The dropping funnel was charged with the solution of aluminum trichloride in diethyl ether.

The aluminum trichloride solution was added at a rate that allowed for a gentle reflux of the reaction (24 drops/sec).

When reaction was complete, there was no more heat release and the reaction mixture returned to starting temperature (about 20° C.).

The completed reaction was filtered through a medium frit to remove the solid lithium chloride byproduct.

The 1-methylpyrrolidinealane (MPA) product was distilled to remove the solvent.

A second distillation was performed at reduced pressure to ensure MPA product purity.

The MPA yield was 76% based on aluminum.

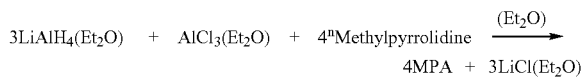

The invention claimed is:

1. A process for preparing an organometallic compound represented by the formula $H_3Al:L_n$ wherein L is one or more Lewis bases capable of providing an unshared electron pair to the aluminum and n is 1 or 2, said process selected from the following:
   (1) a process for preparing said organometallic compound comprising (a) forming a first solution of an alkali metal aluminum hydride and a Lewis base in an ethereal solvent, (b) adding to said first solution an aluminum halide in an ethereal solvent under reaction conditions sufficient to produce a second solution comprising said organometallic compound, and (c) separating said organometallic compound from said second solution;
   (2) a process for preparing said organometallic compound comprising (a) forming a first solution of an aluminum halide and a Lewis base in an ethereal solvent, (b) adding to said first solution an alkali metal aluminum hydride in an ethereal solvent under reaction conditions sufficient to produce a second solution comprising said organometallic compound, and (c) separating said organometallic compound from said second solution; and
   (3) a process for preparing said organometallic compound comprising (a) reacting an aluminum halide and an alkali metal aluminum hydride in the presence of an ethereal solvent and under reaction conditions sufficient to produce a first solution, (b) adding to said first solution a Lewis base optionally in an ethereal solvent under reaction conditions sufficient to produce a second solution comprising said organometallic compound, and (c) separating said organometallic compound from said second solution.

2. The process of claim 1 wherein the ethereal solvent comprises diethyl ether, diisopropyl ether, di-n-propyl ether, di-n-butyl ether and tetrahydrofuran.

3. The process of claim 1 wherein the alkali metal aluminum hydride is selected from lithium aluminum hydride and sodium aluminum hydride.

4. The process of claim 1 wherein the aluminum halide is selected from aluminum chloride, aluminum bromide, aluminum iodide and aluminum fluoride.

5. The process of claim 1 wherein the Lewis base comprises thiophene, thiopyran or a cyclic organic amine.

6. The process of claim 5 wherein the cyclic organic amine is selected from an alkylaziridine, alkylazetidine, alkylpyrrolidine, alkylpiperidine, alkylhexamethyleneimine, alkylheptamethyleneimine and alkylpiperazine.

7. The process of claim 5 wherein the cyclic organic amine is selected from 1-methylpyrrolidine, 1-butylpyrrolidine, 1,4-dimethylpyrrolidine, 1-methylpiperidine, 1-ethylpiperidine, 1,2,2,6,6-pentamethylpiperidine, 1,4-dimethylpiperazine, thiophene and thiopyran.

8. The process of claim 5 wherein the cyclic organic amine is 1-methylpyrrolidine.

9. The process of claim 1 wherein the organometallic compound is selected from 1-methylpyrrolidinealane, 1-methylpiperidinealane, 1-ethylpiperidinealane, 4-methylmorpholinealane and 1,4-dimethylpiperazinealane.

10. The process of claim 1 wherein the organometallic compound yield is from about 65 to 99%.

11. The process of claim 1 wherein the organometallic compound yield is from about 75 to 99%.

12. A process for preparing an organometallic compound represented by the formula $H_3Al:L_n$ wherein L is one or more Lewis bases capable of providing an unshared electron pair to the aluminum and n is 1 or 2, said process comprising (a) forming a first solution of an alkali metal aluminum hydride and a Lewis base in an ethereal solvent, (b) adding to said first solution an aluminum halide in an ethereal solvent under reaction conditions sufficient to produce a second solution comprising said organometallic compound, and (c) separating said organometallic compound from said second solution.

13. The process of claim 12 wherein the ethereal solvent comprises diethyl ether, diisopropyl ether, di-n-propyl ether, di-n-butyl ether and tetrahydrofuran.

14. The process of claim 12 wherein the organometallic compound yield is from about 65 to 99%.

15. A process for preparing an organometallic compound represented by the formula $H_3Al:L_n$ wherein L is one or more Lewis bases capable of providing an unshared electron pair to the aluminum and n is 1 or 2, said process comprising (a) forming a first solution of an aluminum halide and a Lewis base in an ethereal solvent, (b) adding to said first solution an alkali metal aluminum hydride in an ethereal solvent under reaction conditions sufficient to produce a second solution comprising said organometallic compound, and (c) separating said organometallic compound from said second solution.

16. The process of claim 15 wherein the ethereal solvent comprises diethyl ether, diisopropyl ether, di-n-propyl ether, di-n-butyl ether and tetrahydrofuran.

17. The process of claim 15 wherein the organometallic compound yield is from about 65 to 99%.

18. A process for preparing an organometallic compound represented by the formula $H_3Al:L_n$ wherein L is one or more Lewis bases capable of providing an unshared electron pair to the aluminum and n is 1 or 2, said process comprising (a) reacting an aluminum halide and an alkali metal aluminum hydride in the presence of an ethereal solvent and under reaction conditions sufficient to produce a first solution, (b) adding to said first solution a Lewis base optionally in an ethereal solvent under reaction conditions sufficient to produce a second solution comprising said organometallic compound, and (c) separating said organometallic compound from said second solution.

19. The process of claim 18 wherein the ethereal solvent comprises diethyl ether, diisopropyl ether, di-n-propyl ether, di-n-butyl ether and tetrahydrofuran.

20. The process of claim 18 wherein the organometallic compound yield is from about 65 to 99%.

* * * * *